United States Patent [19]
Kikuchi et al.
[11] Patent Number: 4,913,158
[45] Date of Patent: Apr. 3, 1990

[54] ULTRASONIC PROBE FOR MEDICAL DIAGNOSTIC EXAMINATIONS

[75] Inventors: Koh Kikuchi, Ota; Yasuyuki Morita, Yokohama; Yoshiyuki Sugiyama, Ayase, all of Japan

[73] Assignee: Matsushita Electric Industrial Co., Ltd., Osaka, Japan

[21] Appl. No.: 222,394

[22] Filed: Jul. 19, 1988

Related U.S. Application Data

[63] Continuation-in-part of Ser. No. 8,955, Jan. 30, 1987, abandoned.

[30] Foreign Application Priority Data

| | | | |
|---|---|---|---|
| Jan. 30, 1986 | [JP] | Japan | 61-18417 |
| Feb. 18, 1986 | [JP] | Japan | 61-22741 |
| Apr. 1, 1986 | [JP] | Japan | 61-74771 |
| Jun. 6, 1986 | [JP] | Japan | 61-87077 |
| Jul. 16, 1986 | [JP] | Japan | 61-198885 |
| Jul. 18, 1986 | [JP] | Japan | 61-111023 |
| Nov. 18, 1986 | [JP] | Japan | 61-177201 |

[51] Int. Cl.[4] .......... A61B 8/00
[52] U.S. Cl. .......... 128/660.1; 73/633
[58] Field of Search .......... 128/660.09, 660.10, 128/661, 662, 663; 74/426, 427, 436, 459.5; 73/861.25, 628, 633

[56] References Cited

U.S. PATENT DOCUMENTS

| | | | |
|---|---|---|---|
| 1,274,918 | 8/1918 | Maag | 74/427 |
| 3,845,463 | 10/1974 | Timbs | 73/633 |
| 4,232,556 | 11/1980 | Cole | 73/628 |
| 4,330,874 | 5/1982 | Sorwick | 128/660 |
| 4,374,525 | 2/1983 | Baba | 73/633 |
| 4,567,895 | 2/1986 | Putzke | 128/660.1 |
| 4,718,297 | 1/1988 | Hawkins | 74/427 |
| 4,773,426 | 9/1988 | Molnav et al. | 73/633 |

*Primary Examiner*—Francis Jaworski
*Assistant Examiner*—George Manuel
*Attorney, Agent, or Firm*—Wenderoth, Lind & Ponack

[57] ABSTRACT

An ultrasonic probe which scans an ultrasonic beam in a sector area by a mechanical drive is disclosed. The ultrasonic probe essentially has a driving motor, a rotary shaft rotatably supported in a direction perpendicular to the direction of the driving shaft of the driving motor, a rotor shaft rotatably supported in a direction parallel to the direction of the rotary shaft, a rotor mounted on the rotor shaft for carrying ultrasonic transducers, screw gears for transmitting rotation of the motor to the rotary shaft, and a transmitting device for transmitting rotation of the rotary shaft to the rotor.

21 Claims, 9 Drawing Sheets

ULTRASONIC PROBE FOR MEDICAL DIAGNOSTIC EXAMINATIONS

This application is a continuation-in-part of now abandoned application Ser. No. 07/008,955, filed Jan. 30, 1987.

BACKGROUND OF THE INVENTION

The present invention relates to ultrasonic probes particularly for medical diagnostic purposes, and more particularly to ultrasonic probes which scan an ultrasonic beam by a mechanical means.

FIG. 1 shows a conventional mechanical sector-scanning type ultrasonic probe (hereafter referred to as "MSP"). A sub-rotary shaft 106 is rotatably supported at its ends in a frame 101. The sub-rotary shaft 106 is rotated by a motor 102 through motor shaft 103, and bevel gears 104, 105. The rotation of the sub-rotary shaft 106 is transmitted to a rotor shaft 108 through spur gears 107 and 109. The rotor shaft 108 rotates a rotor 110 having ultrasonic transducers 111 for mechanical scanning.

The amount of rotation of the motor 102 is detected by a rotary encoder 112 which controls a driving circuit 113 of the motor 102. Reference numeral 114 designates an oil seal.

In the conventional MSP, the interlocking between the bevel gears 104 and 105 is poor, so that the rotation of the motor 102 cannot be transmitted smoothly to the rotor 110, which causes deterioration of the picture quality of an object.

Furthermore, the bevel gears 104, 105 generate considerable driving noise when meshing. In addition to this, the bevel gears 104, 105 are expensive.

Moreover, the rotation of the sub-rotary shaft 105 cannot be transmitted smoothly to the rotor 110, because of eccentricity of the spur gears 107, 109. The spur gears 107, 109 also generate considerable driving noise when meshing.

SUMMARY OF THE INVENTION

It is therefore an object of the present invention to provide an ultrasonic probe which has a mechanism to transmit the rotation of the motor smoothly to the rotor on which the ultrasonic transducer is mounted.

It is another object of the present invention to reduce manufacturing cost of the ultrasonic probes.

It is a further object of the present invention to provide a sub-rotary shaft and rotor shaft which are easy to assemble.

It is a further object of the present invention to provide an ultrasonic probe with low driving noise.

According to the present invention, an ultrasonic probe is provided which comprises a driving motor, a sub-rotary shaft rotatably supported in a direction perpendicular to the direction of the driving shaft of the driving motor, a rotor shaft rotatably supported in a direction parallel to the direction of the sub-rotary shaft, a rotor mounted on the rotor shaft for carrying an ultrasonic transducer, first screw gear mounted on the driving shaft of the driving motor, second screw gear mounted on the sub-rotary shaft meshing with to the first screw gear, and means for transmitting the rotation of the sub-rotary shaft to the rotor axis. The means are preferably comprised of a pulley mounted on the sub-rotary shaft, a pulley mounted on the rotor shaft, and a belt stretched between the pulleys.

BRIEF DESCRIPTION OF THE DRAWINGS

The present invention will be described in further detail with reference to the accompanying drawings, in which.

The same or corresponding elements and parts are designated by like reference numerals throughout the drawings.

DETAILED DESCRIPTION OF THE INVENTION

Figure 2:
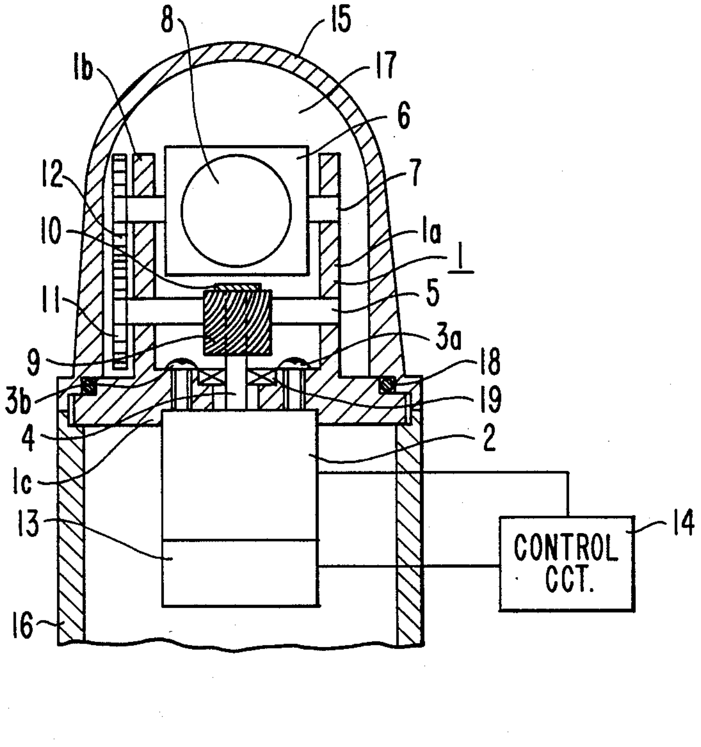
FIG. 2 is a vertical cross-sectional view of an embodiment of the ultrasonic probe in accordance with the present invention.
Figure 3:
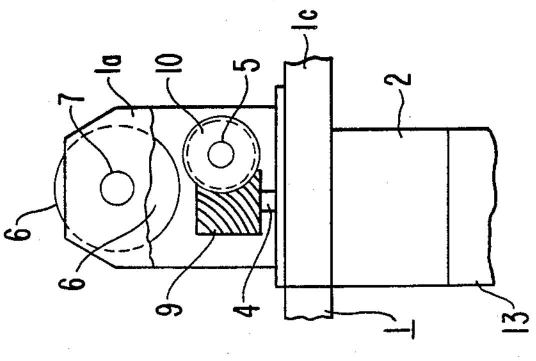
FIG. 3 is a side view of the ultrasonic probe of FIG. 2 without the casing.
Figure 6A:
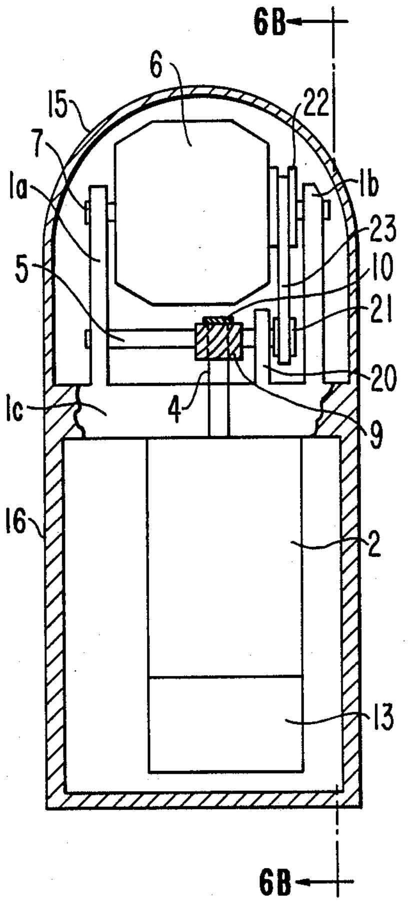
FIG. 6A is a vertical cross-sectional view of a third embodiment of the ultrasonic probe in accordance with the present invention.
Figure 6B:
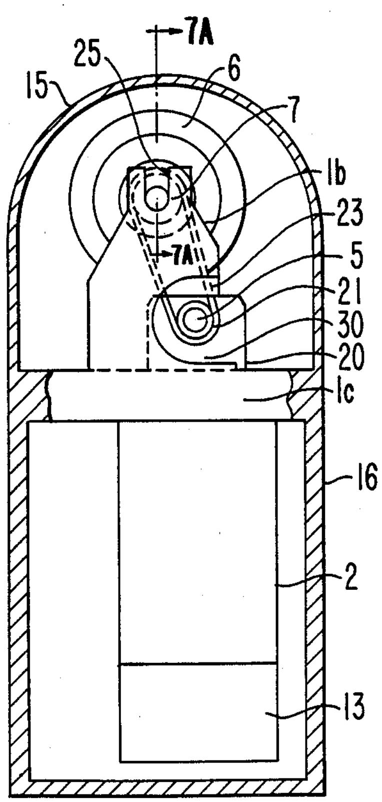
FIG. 6B is a sectional view taken along the line 6B—6B of FIG. 6A.

Referring now the FIGS. 2 and 3, a driving motor 2 is supported on a bottom plate 1C of a metal frame 1 by bolts 3*a*, 3*b*. The metal frame 1 has a pair of supporting frames 1*a*, 1*b* thereon. A sub-rotary shaft 5 is supported at the lower portion of the supporting frames 1*a*, 1*b* perpendicular to the direction of a driving shaft 4 of the driving motor 2. The driving shaft 4 has a screw gear 9 at its top end. The sub-rotary shaft 5 has a screw gear 10 which is meshed with the screw gear 9 of the driving shaft. As can be seen from the relative sizes of the two screw gears in FIGS. 2 and 3, because the gears are nearly the same size, the gear ratio is very small.

The supporting frames 1*a* and 1*b* also support a rotor shaft 7, parallel to the sub-rotary shaft 5, at an upper portion thereof. The rotor shaft 7 supports a rotor 6 on which ultrasonic transduces 8 are mounted. The sub-rotary shaft 5 and rotor shaft 7 are mechanically coupled through spur gears 11 and 12, each is mounted at one end of the corresponding sub-rotary shaft 5 or rotor shaft 7.

The driving motor 2 is coupled to a rotary encoder 13 for detecting rotation of the rotor 6 or ultrasonic transducer 8.

An outer casing 15 of plastic is threaded to a back casing 16 of plastic. Acoustic energy propagating liquid 17 fills the outer casing 15. The liquid 17 is sealed in the casing by 0 ring 18 between the bottom plate 1C and the casing 15, and by oil sealing means 19 between the driving shaft 4 and the bottom plastic plate 1C.

When the driving motor 2 is activated by a control circuit 14, the rotation of the driving shaft 4 of the driving motor 2 is transmited to the sub-rotary shaft 5 through screw gears 9 and 10 to rotate the sub-rotary shaft 5. The rotation of the sub-rotary shaft 5 is similarly transmitted to the rotor shaft 7 through spur gears 11 and 12 to rotate rotor shaft 7. As a result, rotor 6 is rotated and scanning of the ultrasonic transducer is performed.

The screw gears 9 and 10 are always meshed by plural gear teeth with each other, so that the rotation of the motor shaft 4 is smoothly transmitted to the rotor shaft 7, whereby superior picture quality is obtained, and the driving noise of the screw gears is very low. In addition, the teeth of the screw gears 9 and 10 are easy to process in comparsion with bevel gears, which reduces the manufacturing cost of the gears.

Figure 5:
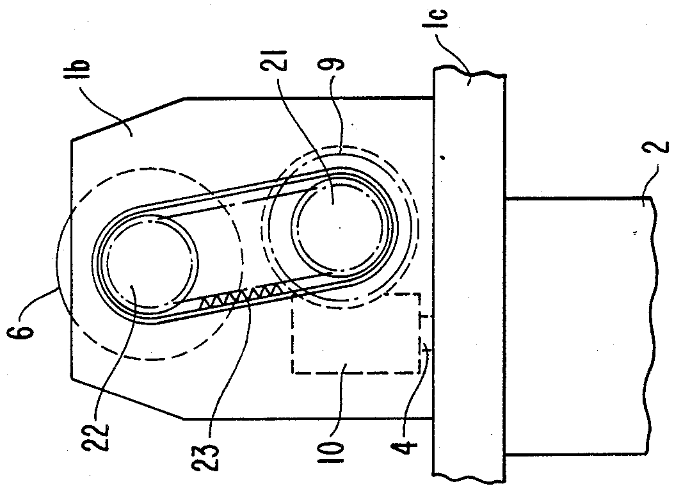
FIG. 5 is a side view of the ultrasonic probe of FIG. 4 without the casing.
Figure 4:
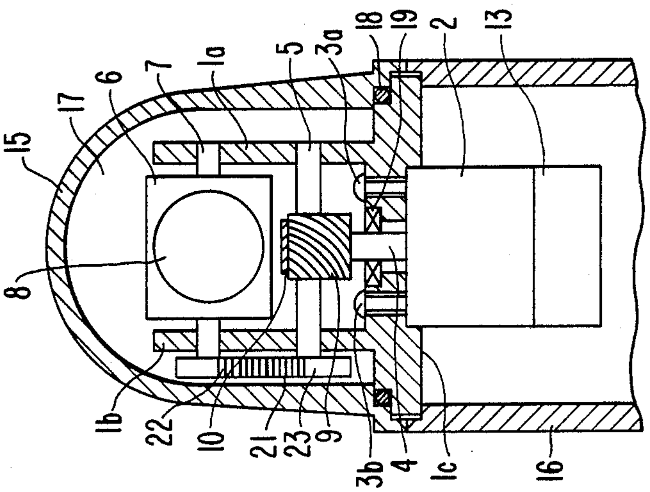
FIG. 4 is a vertical cross-sectional view of another embodiment of the ultrasonic probe in accordance with the present invention.

Referring now to FIGS. 4 and 5, in place of spur gears 11 and 12, a timing pulley 21 is provided at one end portion of the sub-rotary shaft 5. In the same maner, a timing pulley 22 is provided at one end of the rotor shaft 7. The timing pulleys 21 and 22 are coupled with a timing belt 23.

The sub-rotary shaft 5 is rotated by the driving motor 2 through screw gears 9 and 10. The rotation of the sub-rotary shaft 5 is transmitted to the rotor shaft 7 through the timing pulleys 21 and 22, and the timing belt 23. The rotor shaft 7 rotates the rotor 6 to perform scanning of ultrasonic beam emitted from the ultrasonic transducer 8.

Figure 1:
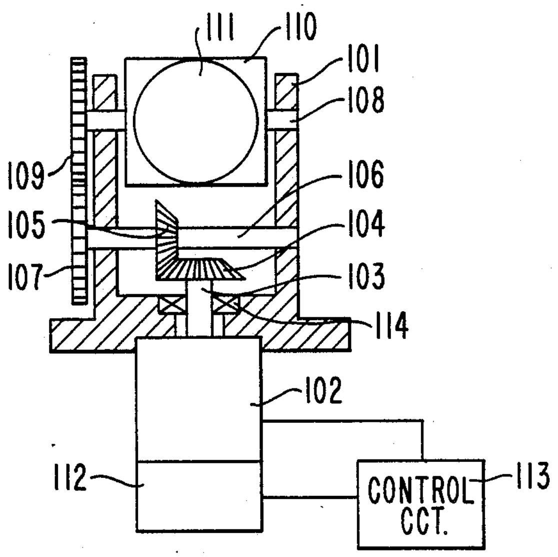
FIG. 1 (PRIOR ART)
FIG. 1 is longitudinal a cross-sectional view of a conventional ultrasonic probes.

As described above, the transmission of the rotation from the sub-rotary shaft to the rotor shaft 7 is achieved indirectly by the flexible timing belt 23. Therefore, any error in the spacing between the sub-rotary shaft 5 and the rotor shaft 7, which may occur in manufacturing, is absorbed by the timing belt 23, so that irregularity of the rotor 6 based on an error of distance between the sub-rotary shaft 5 and the rotor 7, or an eccentricity of the spur gears 107, 109 (see FIG. 1) is avoided. Furthermore, the flexible timing belt 23 reduces driving noise between the timing pulleys 21, 22 and the timing pulleys 23, and makes the rotor axis 7 rotate smoothly for obtaining stable ultrasonic picture information.

Figure 7A:
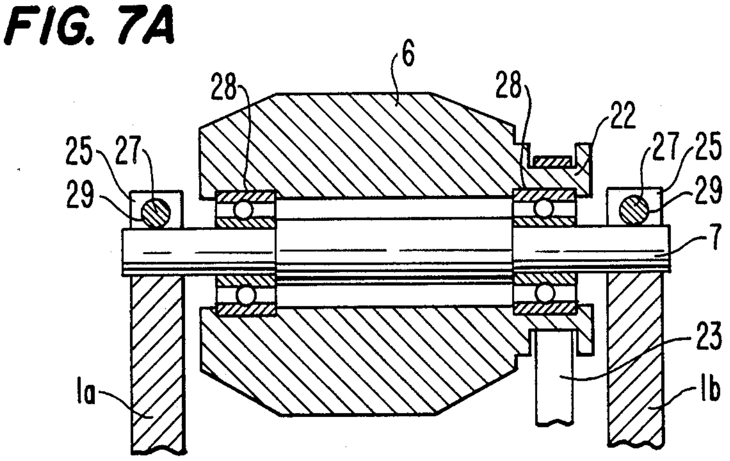
FIG. 7A is a sectional view taken along the line 7A—7A of FIG. 6B.
Figure 7B:
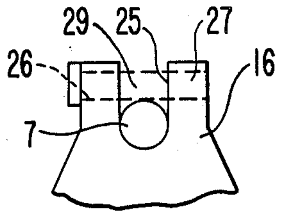
FIG. 7B is a side view of a part of FIG. 7A.

Referring now to FIGS. 6A, 6B, 7A and 7B, a third embodiment of the present invention will be described. A sub-frame 20 is provided near the supporting frame 1*b* between the supporting frames 1*a* and 1*b*. The sub-rotary shaft 5 is rotatably supported between the supporting frame 1*a* and the sub-frame 20. At the top portion of the supporting frames 1*a* and 1*b*, a U-shape notch 25, and screw holes 26, 27 are provided as shown in FIGS. 7A and 7B. The rotor 6 having ultrasonic transducers is rotatably mounted on the rotor shaft 7 through bearings 28. Both ends of the rotor shaft 7 are detachably mounted in the U-shaped notches 25 and are held in place by screws 29 inserted into the screw holes 26 and 27. At one end of the sub-rotary shaft 5, a pulley 21 without a rim is furnished between the supporting frame 1*b* and sub-frame 20. The pulley 21 is coupled with a pulley 22 on the rotor 6 and having a rim around the rotor shaft 7 through the timing belt 23. The supporting frame 1*b* has an aperture 30 having a diameter larger than that of the pulley 21. The embodiment makes it possible to put the timing belt 23 on the pulleys 21 and 22 and remove it therefrom, because the rotor shaft is detachable from the supporting frames 1*a* and 1*b* by removing the screws 29, and the aperture 30, through which putting on and off the timing belt 23 is performed, is provided. It is also easy to put the timing belt 23 on the pulley 21 and remove it therefrom because pulley 21 has no rim.

Figure 8:
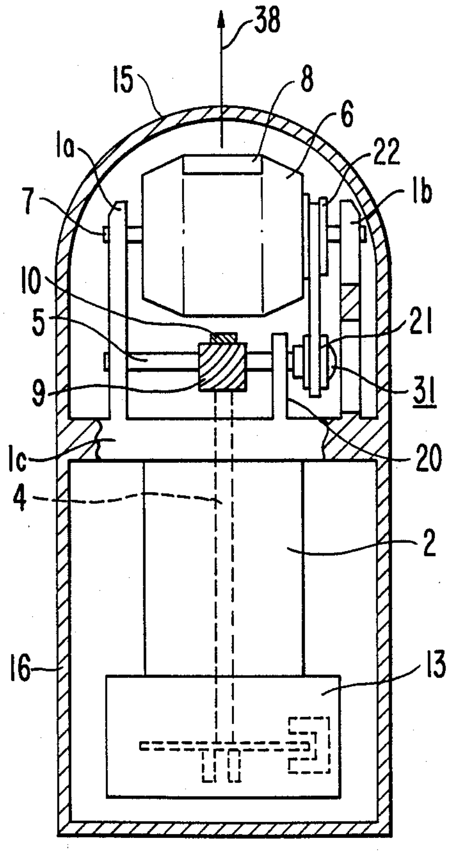
FIG. 8 is a longitudinal cross-sectional view of fourth embodiment of the ultrasonic probe in accordance with the present invention.

FIG. 8 illustrates a fourth embodiment of the present invention. In FIG. 8, the same parts and elements as those of FIG. 6 are labeled with the same reference numerals.

Figure 9:
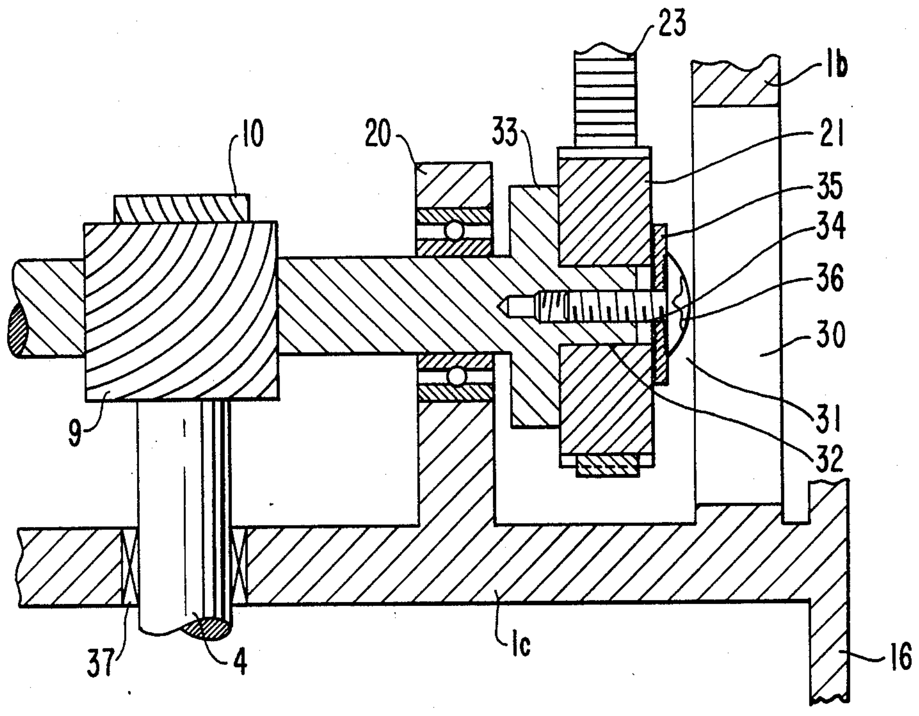
FIG. 9 is a cross-sectional view on an enlarged scale of a part of the ultrasonic probe of FIG. 8.

The embodiment is different from that of FIG. 6 in the nature of the attaching portion for attaching pulley 21 to the sub-rotary shaft 5. In FIG. 8, the pulley 21 is attached to the sub-rotary axis 5 by an attaching member 31 adjustable in the rotary direction. The attaching member 31 will be explained detail in connection with FIG. 9. One end portion of the sub-rotary shaft 5 is supported by the sub-frame 20 and at the end of the sub-rotary shaft outside sub-frame 20, a flange member 33, a supporting portion 32, and a threaded hole 34 are provided. The pulley 21 is mounted on the supporting portion 32, and fixed between the flange member 33 and a washer 35 which is clamped by a bolt 36 inserted into the hole 34 of the sub-rotary shaft 5. The timing belt 23 is mounted between the pulley 21 and the pulley 22 on the rotor shaft 7. The aperture 30 has a diameter larger than that of the pulley 21 and extends through the supporting frame 1*b* at the position corresponding to the pulley 21. Reference numeral 37 designates a seal member provided between the motor driving shaft 4 and the bottom plate 1C of the frame 1.

The direction of emission 38 of the ultrasonic beam from the ultrasonic transducer 8 is able to be detected by the signal from the rotary encoder 13. Therefore, the angle at which the pulley 21 is attached to the sub-rotary shaft 5 can be adjusted as follows. When assembling of the ultrasonic probe is finished, the bolt 36 is loosened by a tool inserted through the aperture 30, and driving motor 2 is rotated. When the rotary encoder 13 generates a predetermined signal, the driving motor 2 is stopped, and the pulley 21 is rotated by hand to a certain position where the direction of emission of the ultrasonic beam 38 is coincident to the predetermined direction, while holding the sub-rotary shaft 5 in a fixed state. Thus adjusted, the pulley 21 is fixed to the sub-rotary shaft 5 by screwing down the bolt 36. As described above, it is possible to manufacture and adjust the direction of emission of the ultrasonic beam in a short time without skill.

FIGS. 10A to 11B illustrate a fifth embodiment especially showing a bearing means for the sub-rotary shaft. The parts and elements which are the same as those of FIG. 6 are labeled with the same reference numerals.

The sub-rotary shaft 5 is rotatably supported on the supporting frame 1*a* and the sub-frame 20 by radial bearings 43 and 44. The sub-rotary shaft 5 has, within the inner wall of the radial bearing 43 and radial bearing 44, stepped end portions 5*a* and 5*b*. A rim 44*a* of the radial bearing 44 is engaged with the inner surface of the sub-frame 20 to regulate one directional thrusting of the sub-rotary shaft 5. A supporting member 45 is slidably mounted in the supporting frame 1*a* at the outer end of the stepped portion 5*a* of the sub-rotary shaft 5. The supporting member 45 is composed of a circular plate 46, ring portion 47 and a projection 48 on the circular plate 46. A leaf spring 49 is attached to the supporting frame 1*a* by a screw 50. The leaf spring 49 pushes on the projection 48 of the supporting member 45 to regulate the position of the radial bearing 43.

When the motor 2 is driven, the sub-rotary shaft 5 undergoes bi-directional thrusting load along its anial direction which is liable to oscillate the sub-rotary shaft 5. However, the brim 44 and the leaf spring 49 prevent the oscillation of the sub-rotary shaft 5 to lower the vibration and driving noise of the ultrasonic probe. The leaf spring 49 also operates as a safety device for absorbing shock. The width of the ring portion 47 of the supporting member can be made small so that the supporting frame 1*a* can be made thin. As a result, the radius $r_1$ of the front casing 15 can be made small to provide a slender ultrasonic probe. The slender ultrasonic probe can widen the observation area in a human body by pushing the probe between ribs of the human body.

Figure 15:
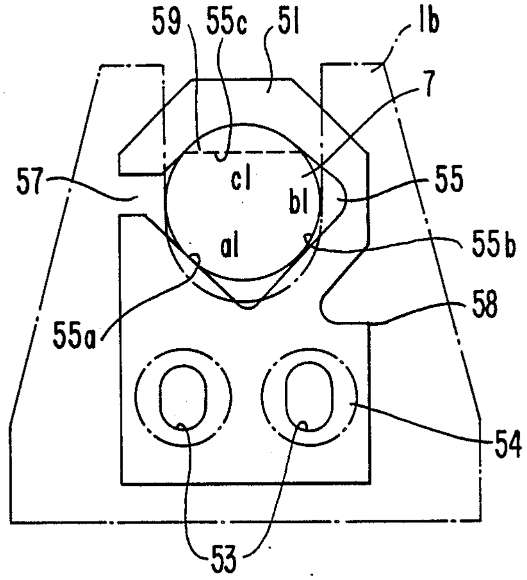
FIG. 15 is a side view of the part of FIG. 14.
Figure 16:
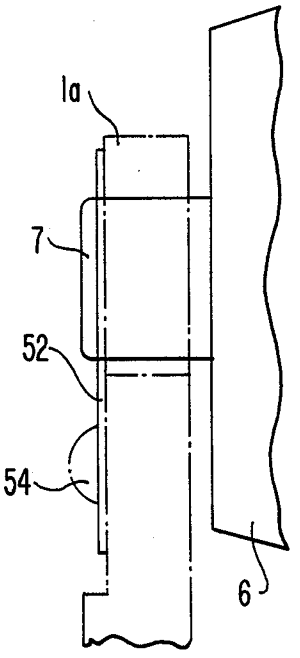
FIG. 16 is a front view on an enlarged scale of another part of the ultrasonic probe of FIG. 12.
Figure 17:
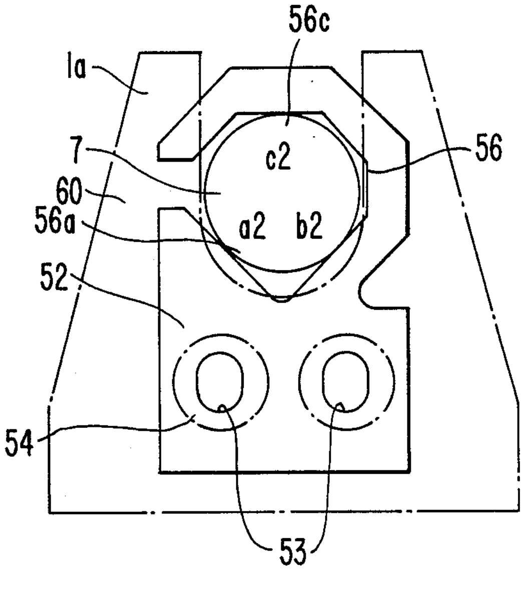
FIG. 17 is a side view of the part of FIG. 16.

FIGS. 12 to 17 illustrate a sixth embodiment of a part of the bearing portion of the rotor shaft according to the present invention. The parts and elements which are the same as those of FIG. 2 are labelled with the same reference numerals. At the top end portion of the supporting frame 1*b*, a supporting plate 51 is adjustably mounted by screws 54 through oblong holes 53 as shown in FIG. 15. In the same manner, a supporting plate 52 is adjustably mounted on the supporting frame 1*a* by screws 54 through oblong holes 53 as shown in FIG. 17. Each of the supporting plates 51 and 52 is made of stainless steel leaf spring member, and apertures 55, 56 are provided at the top portion thereof.

The periphery of the aperture 55 has a V-shaped portion 55*a*, 55*b* and a straight portion 55*c* which is at an equal angle to each of the V-shaped portion 55*a*, 55*b* as shown in FIG. 15. One side of the aperture 55 is cut out to make an opening portion 57. A cut portion 58 is provided on the outside of one peripheral portion 55*a* of the V-shaped portion 55*a*, 55*b*.

The rotor shaft 7 has a groove 59 having a straight bottom at one end portion thereof. The width of the groove 59 is same as the thickness of the supporting plate 51. This end of the rotor shaft 7 is inserted into the aperture 55 in such a manner that the groove 59 engages with the straight portion 55C of the aperture 55. The V-shaped portion 55*a*, 55*b* contacts the outer periphery of the rotor shaft 7 at points $a_1$ and $b_1$, and the straight portion 55C contacts the straight bottom of the groove 59. The contacted straight portion $C_1$ pushes the rotor shaft 7 against the contacted points $a_1$ and $b_1$ by a spring tension of the opening portion 57. As a result, the rotor shaft 7 is supported in a locked state. The spring tension is adjustable by providing the cut portion 58.

Likewise, as shown in FIG. 17, the periphery of the aperture 56 has a V-shaped portion 56*a*, 56*b*, which is almost same as the V-shaped portion 55*a*, 55*b* mentioned above, and a straight portion 56C at an equal angle with each of the V-shaped portions 56*a*, 56*b*. An opening portion 60 and a cut portion 61 are also provided the same as the supporting plate 51 of FIG. 15.

The other end of the rotor shaft 7 is inserted into the aperture 56 in such a manner that the V-shaped portions 56*a*, 5*b* and the straight portion 56C contact to the outer pheriphery of the rotor shaft 7 at points $a_2$, $b_2$ and $c_2$ respectively. The contacted point $c_2$ pushes the rotor shaft 7 to the contacted points $a_2$ and $b_2$ by the spring tension of the opening portion 60 to support the rotor shaft 7 in lock state. The spring tension is also adjustable by the cut portion 61. This supporting means can absorb thermal expansion of the rotor shaft 7 the axial direction.

The supporting plates 51 and 52 are thin. Therefore, diameter $D_1$ of the front casing 15, inner radius $r_1$ of the front casing 15, and distance $L_1$ between the rotor 6 and inner top surface of the front casing 15 can be made small. This provides a wide observation area the same as the embodiment of FIGS. 10A to 11B.

Figure 18:
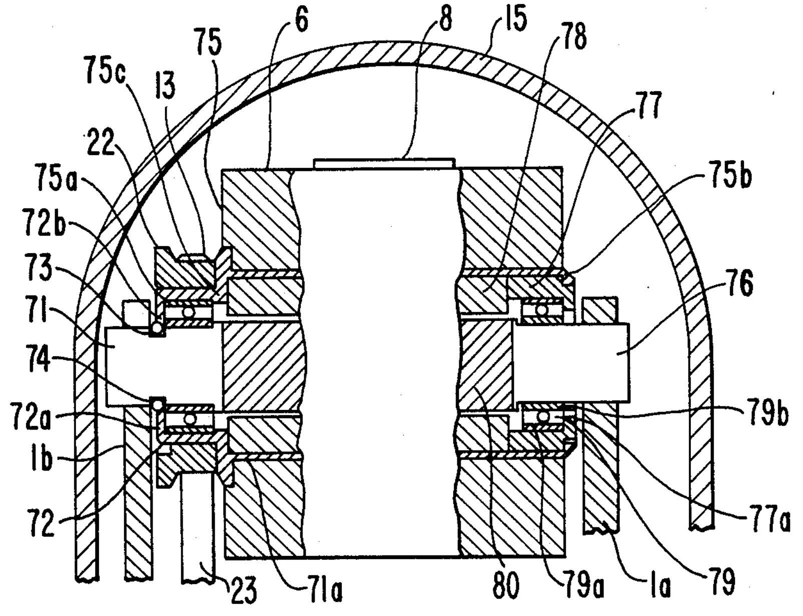
FIG. 18 is a vertical cross-sectional front view of a part of a seventh embodiment of the ultrasonic probe in accordance with the present invention.
Figure 10A:
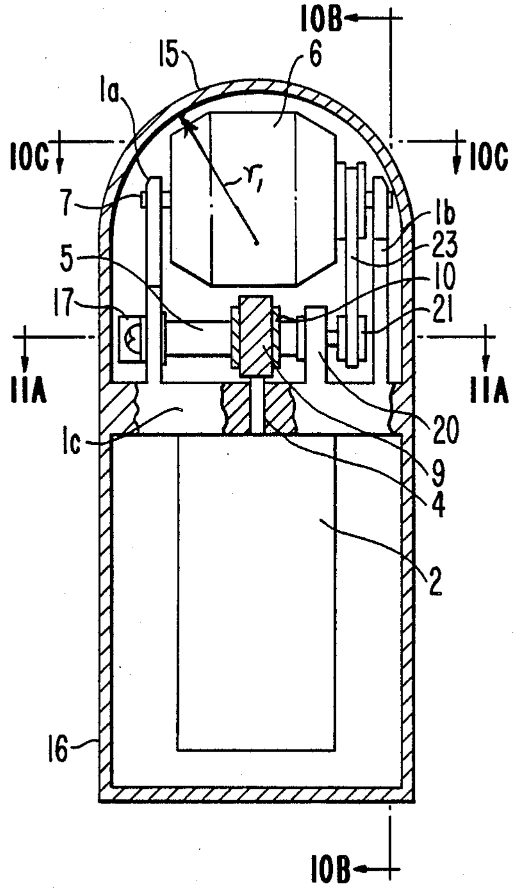
FIG. 10A is a vertical cross-sectional view of a fifth embodiment of the ultrasonic probe in accordance with the present invention.
Figure 10B:
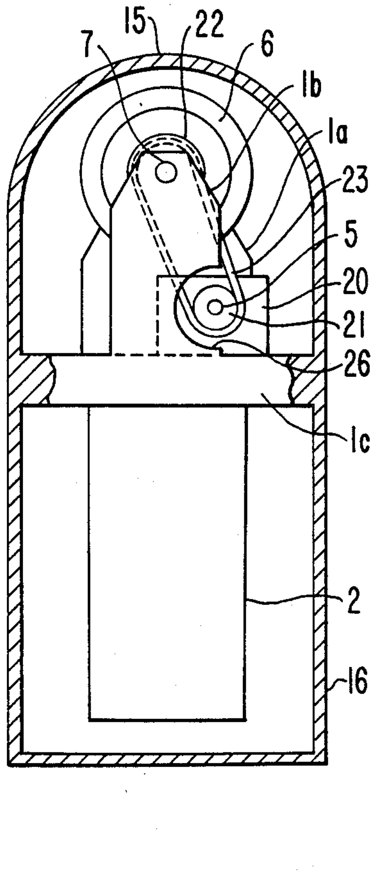
FIG. 10B is a sectional view taken along the line 10B—10B of FIG. 10A.
Figure 11B:
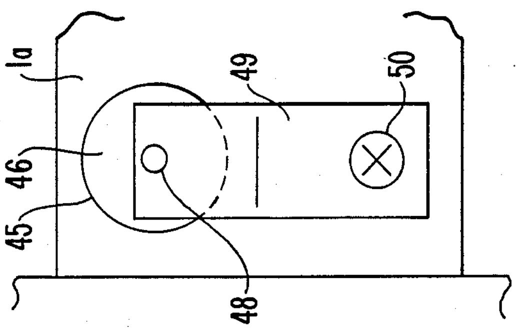
FIG. 11B is a side view of a part of FIG. 11A.
Figure 11A:
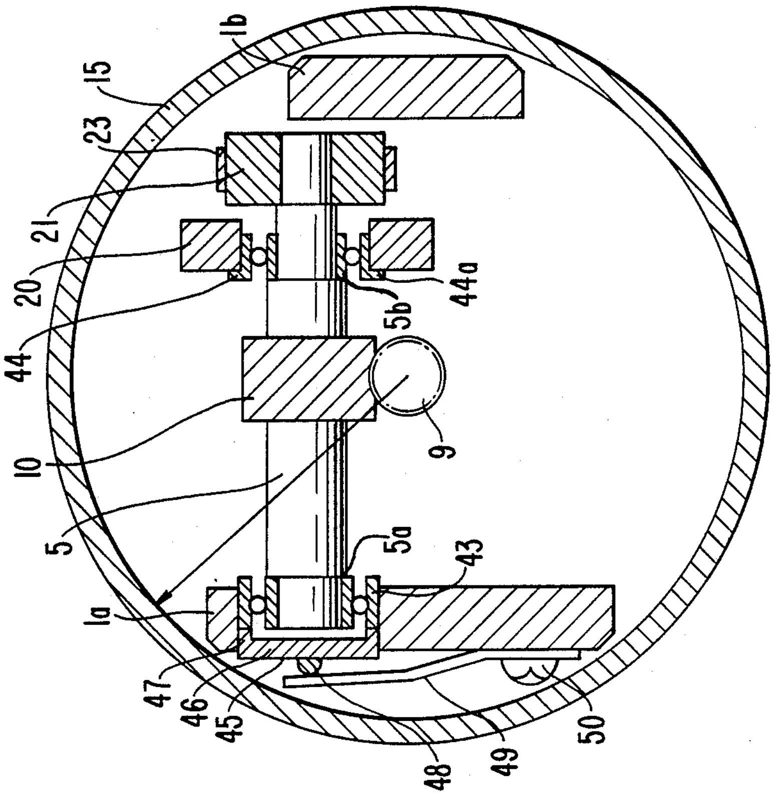
FIG. 11A is a sectional view on an enlarged scale taken along the line 11A—11A of FIG. 10A.
Figure 10C:
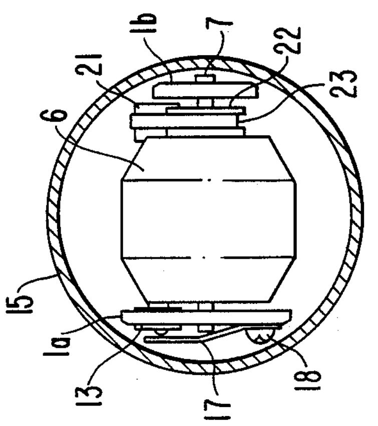
FIG. 10C is a sectional view taken along the line 10C—10C of FIG. 10A.
Figure 12:
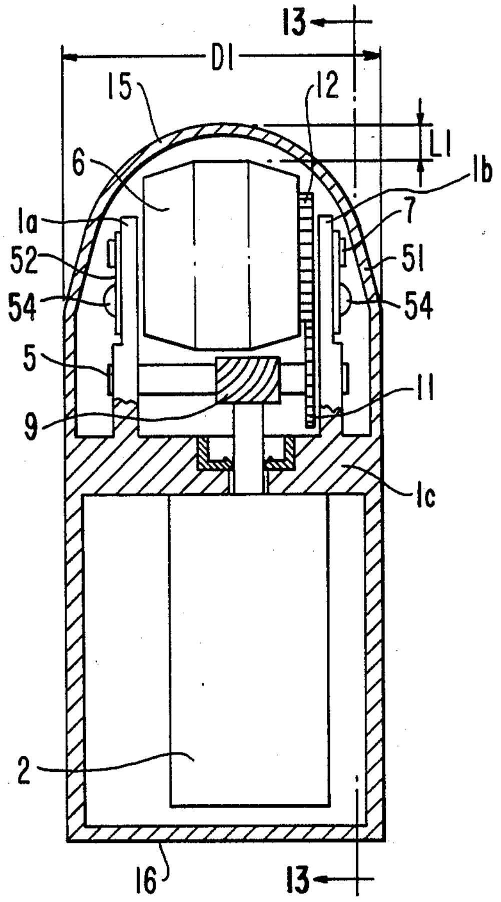
FIG. 12 is a vertical cross-sectional view of a sixth embodiment of the ultrasonic probe in accordance with the present invention.
Figure 13:
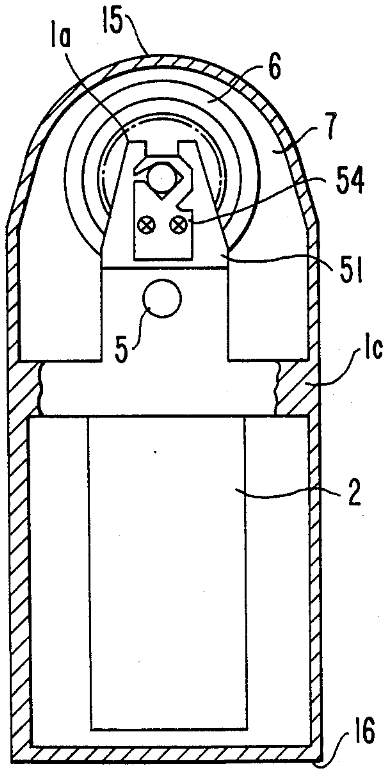
FIG. 13 is a sectional view taken along the line 13—13 of FIG. 12.
Figure 14:
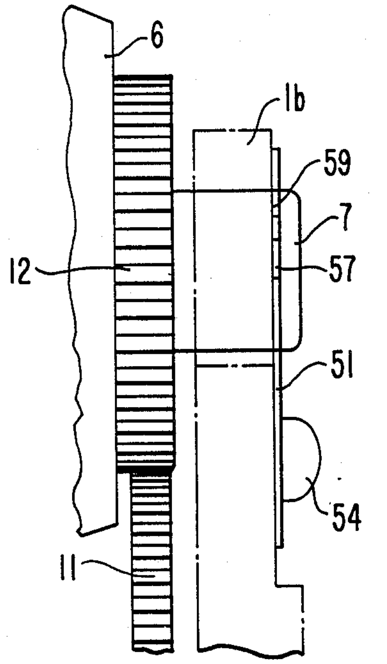
FIG. 14 is a front view on an enlarged scale of a part of the ultrasonic probe of FIG. 12.

Referring now to FIG. 18, another embodiment of the bearing portion of the rotor shaft will be described.

The outer surface of a rotor shaft 71, a groove 73 is provided in which an elastic ring having a cut portion is inlaid. An outer ring 72*a* of a bearing 72 is sandwiched between a stepped portion 75*c* of a transholder 75 and a calkin 75*a* of the transholder 75. An inner ring 72*b* of the bearing 72 is sandwiched between a stepped portion 71*a* of the rotor shaft 71 and the elastic ring 74. Thus the bearing 72 is fixed.

A bearing holder 77 is inserted into the inner side of the transholder 75 in such a manner that the bearing holder 77 is sandwiched between a calkin 75*b* of the transholder 75 and outer core 78. A bearing 79 is disposed between the bearing holder 77 and a rotor shaft 76. An outer ring 79*a* of the bearing holder 79 is held on a projected portion 77*a* of the bearing holder 77, and movable in the axial direction against the rotor shaft 76 and the bearing holder 77. Therefore, the bearing 79 is movable along the inner surface of the bearing holder 77. As a result, no thrusting load is imposed on the bearings 72 and 79, so that the rotor 6 can rotate smoothly, and the bearings 72 and 79 will have a long life.

What is claimed is:

1. An ultrasonic probe comprising:
   - a motor having a driving shaft;
   - first and second supporting frames;
   - a rotary shaft rotatably supported between said first and second supporting frames in a direction perpendicular to the direction of said driving shaft of said motor, and first and second bearing means in said supporting frames in which said rotary shaft is supported:
   - a rotor shaft rotatably supported between said first and second supporting frames in a direction parallel to the direction of said rotary shaft, and third and fourth bearing means in said supporting frames in which said rotor shaft is supported;
   - a rotor having a surface and through the center of which rotor said rotor shaft extends and rotatable with said rotor shaft;
   - ultrasonic transducing means mounted on the surface of said rotor;

screw gear means mechanically coupling said driving motor and said rotary shaft for transmitting rotation of said driving shaft to said rotary shaft and reducing the speed of said rotary shaft from the speed of said driving rotor to a desired speed; and transmitting means coupling said rotary shaft and said rotor shaft for transmitting rotation of said rotary shaft to said rotor shaft.

2. An ultrasonic probe comprising:

a motor having a driving shaft;

first and second supporting frames;

a rotary shaft rotatably supported between said first and second supporting frames in a direction perpendicular to the direction of said driving shaft of said motor, and first and second bearing means in said supporting frames in which said rotary shaft is supported;

a rotor shaft rotatably supported between said first and second supporting frames in a direction parallel to the direction of said rotary shaft, and third and fourth bearing means in said supporting frames in which said rotor shaft is supported;

a rotor having a surface and through the center of which said rotor shaft extends and rotatable with said rotor shaft;

ultrasonic transducing means mounted on the surface of said rotor;

screw gear means mechanically coupling said driving motor and said rotary shaft for transmitting rotation of said driving shaft to said rotary shaft and reducing the speed of said rotary shaft and reducing the speed of said rotary shaft from the speed of said driving rotor to a desired speed; and a pair of spur gears, one spur gear mounted on said rotary shaft and the second spur gear mounted on said rotor shaft, said spur gears being coupled with each other for transmitting rotation of said rotary shaft to said rotor shaft.

3. An ultrasonic probe as claimed in claim 2, wherein each of said third and fourth bearing means comprises a notch for supporting said rotor shaft therein, and detachable means on said supports for holding said rotor shaft in said notches.

4. An ultrasonic probe as claimed in claim 2, further comprising a pair of supporting plates made of leaf spring material, one supporting plate mounted on each of said first and second supporting frames and each supporting plate having an aperture therethrough, and the ends of said rotor shaft extending through the apertures in the respective supporting plates.

5. An ultrasonic probe as claimed in claim 4, wherein one of said apertures has a shape for being contacted by said rotor shaft at three positions on the outer surface of said rotor shaft.

6. An ultrasonic probe as claimed in claim 4, wherein one end portion of said rotor shaft has a groove thereacross, and a part of said plate along the periphery of one of said apertures is inserted in said groove.

7. An ultrasonic probe as claimed in claim 2, wherein said first and second bearing means are fixed on said rotary shaft, and wherein said first bearing means is slidable in said first supporting frame toward the direction of said second bearing means, a supporting member slidably mounted in said first supporting frame and engaging said first bearing means, a leaf spring engaging said supporting member for urging said supporting member toward said second bearing means, and said second bearing means having a rim therein engaging the face of said second supporting frame which faces toward said first supporting frame for regulating the position of said rotary shaft.

8. An ultrasonic probe as claimed in claim 2, further comprising a transholder on said rotor and holding said third bearing means between said transholder and said rotor/shaft, and a ring member fixed to inner portion of said transholder and holding said fourth bearing means between said ring member and said rotor shaft.

9. An ultrasonic probe comprising:

first and second supporting frames;

a motor having a driving shaft;

a rotary shaft rotatably supported between said first and second supporting frames in a direction perpendicular to the direction of said driving shaft of said motor, and first and second bearing means in said supporting frames in which said rotary shaft is supported;

a rotor shaft rotatably supported between said first and a third supporting frames in a direction parallel to the direction of said rotary shaft, and third and fourth bearing means in said supporting frames in which said rotor shaft is supported;

a rotor through the center of which said rotor shaft extends and rotatable with said rotor shaft;

ultrasonic transducing means mounted on the surface of said rotor;

transmitting means coupled between said driving shaft and said rotary shaft for transmitting rotation of said driving shaft to said rotary shaft;

a first timing pulley attached to said rotary shaft;

a second timing pulley attached to said rotor shaft; and a timing belt stretched around and coupled with said first and second pulleys.

10. An ultrasonic probe comprising:

first and second supporting frames;

a motor having a driving shaft;

a rotary shaft rotatably supported between said first and second supporting frames in a direction perpendicular to the direction of said driving shaft of said motor, and first and second bearing means in said supporting frames in which said rotary shaft is supported;

a rotor shaft rotatably supported between said first and second supporting frames in a direction parallel to the direction of said rotary shaft, and third and fourth bearing means in said supporting frames in which said rotor shaft is supported;

a rotor through the center of which said rotor shaft extends and rotatable with said rotor shaft;

ultrasonic transducing means mounted on the surface of said rotor;

a first screw gear attached to said driving shaft and a second screw gear attached to said rotary shaft and meshed with said first screw gear for transmitting rotation of said driving shaft to said rotary shaft;

a first timing pulley attached to said rotary shaft;

a second timing pulley attached to said rotor shaft; and a timing belt stretched around and coupled with said first and second pulleys.

11. An ultrasonic probe as claimed in claim 10, further comprising a third supporting frame disposed between said first and second supporting frames, said first timing pulley being disposed between said second and third supporting frames, and said second timing pulley is disposed between said rotor and said second supporting frame.

12. An ultrasonic probe as claimed in claim 11, wherein said second supporting frame has an aperture opposite said first pulley with a diameter larger than that of said first pulley.

13. An ultrasonic probe as claimed in claim 11, further comprising adjusting means for adjusting the rotational position of said first timing pulley around said rotary shaft, said adjusting means comprising a supporting rod coaxially disposed at one end of said rotary shaft, a flange member disposed between said rotary shaft and said supporting rod, a washer plate for holding said first timing pulley between said flange member and said washer plate, and a screw inserted into said supporting rod through said washer plate.

14. An ultrasonic probe as claimed in claim 10, wherein each of said third and fourth bearing means comprises a notch for supporting said rotor shaft therein, and detachable means on said supports for holding said rotor shaft in said notches.

15. An ultrasonic probe as claimed in claim 10, further comprising a pair of supporting plates made of leaf spring material, one supporting plate mounted on each of said first and second supporting frames and each supporting plate having an aperture therethrough, and the ends of said rotor shaft extending through the apertures in the respective supporting plates.

16. An ultrasonic probe as claimed in claim 15, wherein one of said apertures has a shape for being contacted by said rotor shaft at three positions on the outer surface of said rotor shaft.

17. An ultrasonic probe as claimed in claim 15, wherein one end portion of said rotor shaft has a groove thereacross, and a part of said plate along the periphery of one of said apertures is inserted in said groove.

18. An ultrasonic probe as claimed in claim 10, wherein said first and second bearing means are fixedly mounted on said rotary shaft, and wherein said first bearing means is slidable in said first supporting frame toward the direction of said second bearing means, a supporting member slidably mounted in said first supporting frame and engaging said first bearing means, a leaf spring engaging said supporting member for urging said supporting member toward said second bearing means, and said second bearing means having a rim therein engaging the face of said second supporting frame which faces toward said first supporting frame for regulating the position of said rotary shaft.

19. An ultrasonic probe as claimed in claim 10, further comprising a transholder on said rotor and holding said third bearing means between said transholder and said rotor/shaft, and a ring member fixed to inner portion of said transholder and holding said fourth bearing means between said ring member and said rotor shaft.

20. An ultrasonic probe as claimed in claim 10, wherein said first timing pulley is a rimless pulley.

21. An ultrasonic probe comprising:

a rotor having an outer surface and an inner surface;

ultrasonic transducer means mounted on the outer surface of said rotor;

a transholder on said inner surface of said rotor, said transholder having a stepped portion and a first calkin extending axially from said stepped portion on one end thereof and a second calkin on the other end thereof;

a rotor shaft for rotatably supporting said rotor and said transholder and having a stepped portion at one end thereof adjacent the stepped portion of said transholder and a reduced diameter portion extending into said calkin;

a first bearing member on said reduced diameter portion and having an outer member held between the inner side of said stepped portion of said transholder and said calkin;

the peripheral surface of said reduced diameter portion having a groove therein and a ring member in said groove; said first bearing member having an inner member held between the stepped portion of said rotor shaft and said ring member;

a second bearing member through which the other end of said rotor shaft extends; and a bearing holder inside said second calkin of said transholder and holding said second bearing in said transholder.

* * * * *